United States Patent [19]
Shibuya et al.

[11] Patent Number: 6,060,255
[45] Date of Patent: *May 9, 2000

[54] TYPE IV COLLAGEN HIGH MOLECULAR FORM AND PRODUCTION AND DIAGNOSTIC USE THEREOF

[75] Inventors: Akitaka Shibuya, Sagamihara; Shunji Saitoh, Machida; Toshio Takahashi; Naoko Maruo, both of Yokohama, all of Japan

[73] Assignees: Tosoh Corporation, Yamaguchi-ken; Morinaga & Co., Ltd., Tokyo, both of Japan

[*] Notice: This patent is subject to a terminal disclaimer.

[21] Appl. No.: 09/164,461

[22] Filed: Oct. 1, 1998

[30] Foreign Application Priority Data

Oct. 3, 1997 [JP] Japan ..................................... 9-270759

[51] Int. Cl.⁷ .................................................. G01N 33/53
[52] U.S. Cl. ........................... 435/7.1; 435/7.92; 435/344; 435/975; 436/518; 436/528; 436/531; 530/323; 530/344; 530/356; 530/387.1; 530/388.85; 530/391.1; 530/846
[58] Field of Search ..................................... 435/7.1, 7.92, 435/7.93, 7.94, 7.95, 344, 975; 436/518, 528, 531; 530/323, 344, 356, 387.1, 388.85, 391.1, 846

[56] References Cited

U.S. PATENT DOCUMENTS

| 5,316,914 | 5/1994 | Oshima et al. | 435/7.94 |
| 5,741,652 | 4/1998 | Shibuya et al. | 435/7.1 |

FOREIGN PATENT DOCUMENTS

| 63-108665 | 5/1991 | Japan . |
| 401370 | 12/1990 | WIPO . |

OTHER PUBLICATIONS

Sage et al., "Structural Studies on Human Type IV Collagen," The Journal of Biological Chemistry, 254(19): 9893–9900 (1979).
Hahn et al., "Distribution Of Basement Membrane Proteins In Normal and Fibrotic Human Liver: Collagen Type IV, Laminin, and Fibronectin," Gut, 21:63–71 (1980).
Risteli et al., "7–S Collagen: Characterization of an Unusual Basement Membrane Structure," Eur. J. Biochem 108: 239–250 (1980).
Risteli et al., "Sensitive Radioimmunoassays for 7 S Collagen and Laminin: Application to Serum and Tissue Studies of Basement Membranes," Analytical Biochemistry 113: 372–378 (1981).
Goding, J.W., "Production and Application of Monoclonal Antibodies in Cell Biology, Biochemistry and Immunology," Monoclonal Antibodies: Principles and Practice, p. 7–10; 250–261 (1983).
Högemann et al. "7 S Collagen: A method for the measurement of serum concentrations in man," Clinica Chemica Acta, 144: 1–10 (1984).

Schuppan et al., "Radioimmunoassay for the Carboxy–terminal Cross–linking Domain of Type IV (Basement Membrane) Procollagen in Body Fluids," J. Clin. Invest. 78: 241–248 (1986).
Obata et al, "One step sandwich enzyme immunoassay for human type IV collagen using monoclonal antibodies," Clinica Chimica Acta 181: 293–304 (1989).
Yamada et al., "Clinical Significance of Serum 7S Collagen in Various Liver Diseases," Clin. Biochem. 25: 467–470 (1992).
Yamada et al., "Heterogeneity of antigens related to 7S domain of type IV collagen in serum: Application to patients with chronic liver disease," Clinica Chimica Acta 212: 73–78 (1992).
Murawaki et al., "Serum Type III Procollagen Peptide, Type IV Collagen 7S Domain, Central Triple–helix of Type IV Collagen and Tissue Inhibitor of Metalloproteinases in Patients with Chronic Viral Liver Disease: Relationship to Liver Histology," Hepatology 20(4): 780–787 (1994).
Suou et al., "Relationship Between Serum and Hepatic 7S Fragments of Type IV Collagen in Chronic Liver Disease," Hepatology 23(5): 1154–1158 (1996).
Murawaki et al., "Comparison of serum 7S fragment of type IV collagen and serum central triple–helix of type IV collagen for assessment of liver fibrosis in patients with chronic viral liver disease," Journal of Hepatology, 24: 148–154 (1996).
(Nippon DPC Corp.) Handling Manual of IV Collagen 7S Kit (with English translation) (1994).
(Daiichi Seiyaku) Handling Manual of IV Collagen Assay Kit (with English translation) (1991).
Matsumoto, E. "Foreknowledge of liver fibrosis: Development of immunoassay system for serum collagen peptides with monoclonal antibody," Wakayama Igaku 39(1):87–106 (1988) English summary.
Sato, S. "Clinical significance of measurement of PIIIP, Laminin P1, Type IV–C and 7S in patients with chronic liver diseases—With special reference to histological findings," Nippon Shokaki Byo Gakkai Shi 89(9):2007–2015 (including English summary section) (1992).

(List continued on next page.)

Primary Examiner—Jeffrey Stucker
Attorney, Agent, or Firm—Jeffrey I. Auerbach; Howrey Simon Arnold & White, LLP

[57] ABSTRACT

A type IV collagen high molecular form having a higher molecular weight than the 7S domain of type IV collagen and including the 7S domain in its structure, is obtained from the supernatant being recovered from a collagen solution digested by pepsin in the following steps;

1) salt precipitating with sodium chloride at a concentration no higher than 1.2 M,
2) dissolving the precipitates,
3) salt precipitating with sodium chloride at a concentration no higher than previous concentration. By reacting a sample with an antibody which reacts with this form, the type IV collagen high molecular form in the sample can be measured to allow diagnosis of the degree of liver fibrosis in patients with liver diseases.

14 Claims, 5 Drawing Sheets

OTHER PUBLICATIONS

Kajikawa et al., "Alterations of serum type IV collagen and 7S domain concentrations after hepatectomy for hepatocellular carcinoma," Kanzo 35(2): 131–136 (1994).

Ichida et al., "Progress in hepatitis C Research, Mutation of Hepatitis Virus, and Reexamination of the Inuyama Classification," 19$^{th}$ Inayama Symposium (with English translation) (1995).

Saitoh et al., "Measurement of serum type IV collagen level in chronic liver disease using new assay systems," Kanzo 37(6): 4:304–12:312 (1996).

TYPE IV COLLAGEN HIGH MOLECULAR FORM AND PRODUCTION AND DIAGNOSTIC USE THEREOF

BACKGROUND OF THE INVENTION

1. Field of Invention

The present invention relates to a type IV collagen high molecular form and to a process for its production. The invention further relates to a method for measuring the type IV collagen high molecular form and to a method of diagnosing the degree of liver fibrosis based on that assay.

2. Related Art

It is well known that liver fibrosis occurs in patients with liver diseases, and is caused by the unbalance between synthesis and degradation of type IV collagen in the liver, leading to excess synthesis rather than degradation. A number of reports have been published on the usefulness of serum type IV collagen determination as an indicator of liver fibrosis, and it is known that type IV collagen level in the serum increases with progression of diseases from chronic hepatitis to liver cirrhosis (Japanese Unexamined Patent Publication No. 8-100000, Saito et al., Liver, Vol.37, No.6, p.304–311). This occurs because the major component of fibrotic regions in the liver is type IV collagen, and therefore serum levels of type IV collagen directly reflect the histological degree of liver fibrosis.

Incidentally, the type IV collagen molecules in the blood are released into the blood during the progression of liver fibrosis, i.e. during the process of synthesis and degradation of type IV collagen in the liver, and they are not uniform in terms of molecular species. This is because the structure of type IV collagen is a network structure composed of the amino terminal 7S domain, the carboxyl terminal NC1 and NC2 regions and an intermediate triple helical region which come together in a helix form, and this structure is partially degraded by collagenase and released into the blood.

According to reports by Murawaki et al. in J. Hepatology, Vol.24, p.148–154, 1996 and Clinica Chimica Acta, 212, p.73–78, (1992) (hereunder, "C.C.A"), when an assay is performed using an antibody which recognizes the 7S domain, primarily 2 major molecular species are detected as type IV collagen in the blood: (1) a high molecular form containing the 7S domain and having a molecular weight higher than that of the 7S domain, and (2) the 7S domain itself. According to the same reports, when the assay is performed using an antibody which recognizes the 7S domain and an antibody which recognizes the triple helical region, a type IV collagen smaller than both (1) and (2) is detected. These facts demonstrate that 3 kind of molecules which have different molecular weights exist as the type IV collagen molecules in serum.

Reports in C.C.A also indicate that these 3 molecular species are present as type IV collagen in the blood of both healthy persons and patients with liver disease. However, during the progression of diseases from chronic hepatitis to liver cirrhosis in patients, the serum level of the high molecular form which contains the 7S domain and has a larger size than that of 7S domain, is notably increased among the 3 molecular species of type IV collagen. This type IV collagen high molecular form is believed to be type IV collagen in almost complete form without any degradation by collagenase, and therefore increases or decreases in the amount of the high molecular form of type IV collagen in the blood are considered to be direct reflections of the increase or decrease in type IV collagen synthesis, while the increase or decrease in the 7S domain or lower molecular size type IV collagen in the blood are considered to reflect the increase or decrease in type IV collagen degradation from fibrotic liver.

However, until now there have been no reports regarding separation and purification of the high molecular form of type IV collagen. Even in the aforementioned reports by Murawaki et al., where the patient serum is separated by gel filtration and a commercially available type IV collagen assay kit is used to determine the reactivity of each fraction, it is merely indicated that antigenicity is also found in the fraction having a higher molecular weight than that of 7S domain.

Although commercially available type IV collagen-assay kits exist which can show the reactivity with the type IV collagen high molecular form, they have high reactivity with the aforementioned 7S domain itself or for the smaller type IV collagen, whereas no kit has been available which allows specific determination of only the type IV collagen high molecular form. Consequently, no assay method has existed which directly reflects the synthesis of type IV collagen in the liver.

Incidentally, a monoclonal antibody (hereunder referred to as "monoclonal antibody 67") which is produced by the hybridoma COL IV-67 (deposited at the National Institute of Bioscience and Human Technology on Sep. 27, 1994 as FERM P-14561, and transferred on Sep. 25, 1995 to a deposit in accordance with the Budapest Treaty, as FERM BP-5240) described in Japanese Unexamined Patent Publication No. 8-100000, has been shown to react specifically with the type IV collagen high molecular form, therefore it was assumed that the type IV collagen high molecular form was present in the immunogen for the monoclonal antibody 67, but the type IV collagen high molecular form could not be consistently obtained by the purification method for the immunogen described in Japanese Unexamined Patent Publication No. 8-100000.

SUMMARY OF INVENTION

It has been demonstrated that the progression of liver fibrosis is caused by an unbalance of synthesis and metabolism of collagen, leading to excessive synthesis of type IV collagen. Consequently, a more direct method for assessing the progression of liver fibrosis would be to measure specifically the high molecular form of type IV collagen which increases markedly in the progression of liver disease and which directly reflects type IV collagen synthesis, without simultaneously measuring the 7S domain or the lower molecular form type IV collagen, both of which are thought to be degradation products of type IV collagen. This would allow more sensitive detection of accelerated synthesis of type IV collagen in the initial stages of liver fibrosis.

It is an object of the present invention to provide a method for obtaining this type IV collagen high molecular form, to measure it in a specific manner, and to provide a method whereby assay of the type IV collagen high molecular form is used for more sensitive and detailed diagnosis of the stages of liver fibrosis.

The present inventors have arrived at the present invention as a result of diligent research on this subject. Specifically, the invention relates to a type IV collagen high molecular form having the following properties:

(a) having a molecular weight higher than that of the 7S domain of type IV collagen;

(b) having the 7S domain in its structure;

(c) being recovered from a collagen solution digested by pepsin in the following steps;

1) salt precipitating with sodium chloride at a concentration no higher than 1.2 M,
2) dissolving the precipitates,
3) salt precipitating with sodium chloride at a concentration no higher than previous concentration, and
4) collecting the supernatant.

The invention further relates to a process for producing the type IV collagen high molecular form, comprising the steps of:

(1) salt precipitating of a collagen solution digested by pepsin with sodium chloride at a concentration no higher than 1.2 M, (2) dissolving the precipitates, (3) salt precipitating again with sodium chloride at a concentration no higher than the previous salt concentration, and then (4) collecting the supernatant to obtain the type IV collagen high molecular form.

The invention still further relates to a method for measuring the type IV collagen high molecular form, comprising the step of reacting an antibody specific to the aforementioned type IV collagen high molecular form with the type IV collagen high molecular form in a sample.

The invention still further relates to a kit used for measuring the type IV collagen high molecular form, comprising an antibody specific to the aforementioned type IV collagen high molecular form.

The invention still further relates to a method for diagnosing the degree of liver fibrosis, using the aforementioned assay method.

The invention still further relates to a method for measuring the type IV collagen high molecular form, comprising the steps of:

(a) measuring the value of type IV collagen high molecular form in a sample, (b) measuring the value of type IV collagen high molecular form in a healthy person, and (c) determining the ratio between (a) and (b).

The invention still further relates to a method for diagnosing the degree of liver fibrosis based on the ratio determined in this manner. The invention will now be explained in more detail.

DETAILED DESCRIPTION

The type IV collagen high molecular form of the invention has a molecular weight higher than that of the 7S domain of type IV collagen. This was confirmed by gel filtration in which the type IV collagen high molecular form was always eluted out prior to the type IV collagen 7S domain. Also, the presence of the 7S domain in the structure was confirmed by its reactivity with a commercially available type IV collagen 7S domain kit (Type IV Collagen/7S Kit, product of Nihon DPC Corporation; hereunder referred to as "kit (A)") (Type IV Collagen/7S Kit User's Manual, Nihon DPC Corporation; Yamada et al., Clin. Biochem. Vol.25, p.467–470, 1992; Risteli et al., Eur. J. Biochem. Vol. 108, p.239–250, 1980).

The type IV collagen high molecular form of the invention is recovered from a collagen solution digested by pepsin in the following steps;

1) salt precipitating with sodium chloride at a concentration no higher than 1.2 M, 2) dissolving the precipitates, 3) salt precipitating with sodium chloride at a concentration no higher than previous concentration, and 4) collecting the supernatant.

There are no particular restrictions on the collagen solution solubilized by pepsin digestion used for the invention, and it may be prepared by a conventional method. For example, it may be obtained according to the method of Sage et al. (J. Biol. Chem. Vol.254, No.19, p.9893–9900, 1979). The collagen solution may also be appropriately purified, if necessary, prior to salt precipitation with the $\leq 1.2$ M sodium chloride. The precipitation with the $\leq 1.2$ M sodium chloride is carried out preferably with 0.5–1.0 M, and more preferably with 0.6–0.8 M sodium chloride. After dissolving the precipitate, the solution sodium chloride concentration was increased up to a concentration no higher than the previous salt concentration, and the supernatant is recovered. There are no particular restrictions on the method of obtaining the type IV collagen high molecular form from the recovered supernatant, and if necessary, it may be accomplished by appropriate salt precipitation, dissolution, dialysis, column chromatography (DEAE-Sepharose, gel filtration, etc.) and similar purification methods. A particularly preferred method of purifying the type IV collagen high molecular form is to obtain the fraction which elutes out prior to the 7S domain by gel filtration.

Most conventional type IV collagen purifications are carried out according to the aforementioned method of Sage et al., whereby a collagen solution solubilized by pepsin digestion is precipitated with 0.7 M sodium chloride and the supernatant is recovered instead of the precipitate, unlike the present invention. According to the invention, however, a collagen solution solubilized by pepsin digestion is precipitated with sodium chloride at a concentration no higher than 1.2 M and the resulting precipitate is recovered, making it possible to obtain type IV collagen of higher molecular weight retaining virtually its complete structure. According to the invention, the precipitation is then repeated with sodium chloride at a concentration lower than the previous salt concentration and the supernatant containing the type IV collagen high molecular form is recovered.

The method of measuring the type IV collagen high molecular form according to the invention is characterized by reacting an antibody specific to the type IV collagen high molecular form with the type IV collagen high molecular form in a sample.

The antibody used here is not particularly restricted so long as it reacts specifically with the type IV collagen high molecular form, and it may be either a monoclonal antibody or polyclonal antibody. The method of preparing the antibody is also not restricted, and it may be prepared using the type IV collagen high molecular form as the immunogen, or using a genetic engineering method. Monoclonal antibody 67 is an example of a monoclonal antibody which reacts specifically with the type IV collagen high molecular form. As mentioned above, this monoclonal antibody is produced by the hybridoma COL IV-67 (deposited at the National Institute of Bioscience and Human Technology on Sep. 27, 1994 as FERM P-14561, and transferred on Sep. 25, 1995 to a deposit in accordance with the Budapest Treaty, as FERM BP-5240).

There are no particular restrictions on the method of reacting the antibody specific for the type IV collagen high molecular form with the type IV collagen high molecular form in a sample, and any known immune reaction system may be employed. Examples include the sandwich assay method and the competitive assay method, and a specific example is a sandwich assay system using the monoclonal antibody 67 described in Japanese Unexamined Patent Publication No. 8-100000 and a polyclonal antibody for type IV collagen.

The reagent used for the assay method of the invention may be in a form of kit. Such a kit contains as a reagent an antibody specific for the type IV collagen high molecular form, and the assay can be accomplished by reacting it with the type IV collagen high molecular form in a sample.

According to the invention it is possible to diagnose the degree of liver fibrosis of patients by reacting the antibody specific to the type IV collagen high molecular form with the type IV collagen high molecular form in a sample to detect the type IV collagen high molecular form. It has been demonstrated that the cause of such liver fibrosis is an unbalance of synthesis and metabolism of collagen, leading to excessive synthesis of type IV collagen. Thus, for a more direct observation of the progression of liver fibrosis, it is important to measure the type IV collagen high molecular form which is believed to directly reflect collagen synthesis and which increases markedly in liver cirrhosis, rather than measuring the 7S domain or lower molecular weight type IV collagen, which are considered to be degradation products of type IV collagen.

Currently, the New Inuyama Classification is used to indicate degrees of liver fibrosis (Progress in Hepatitis C Research: Mutations in the Hepatitis Virus, A Reexamination of the Inuyama Classification; edited by the Inuyama Symposium Records Publication Committee, Chugai Medical, 1996, p.183–188), which establishes the categories of F0: no fibrosis, F1: fibrous portal expansion, F2: bridging fibrosis (portal-portal or portal-central linkage), F3: bridging fibrosis with lobular distortion and F4: liver cirrhosis. It has been found that when the type IV collagen high molecular form is measured in the serum from patients with the stages described above, levels of type IV collagen increased in proportion to the severity of fibrosis, i.e. with progressing of liver fibrosis. Consequently, an assay of the type IV collagen high molecular form in blood according to the invention allows both discrimination and diagnosis of the degree of liver fibrosis.

The invention is also a method for measuring the type IV collagen high molecular form in a sample, comprising the steps of:

(a) measuring the value of type IV collagen high molecular form in the sample, (b) measuring the value of type IV collagen high molecular form in a healthy person, and (c) determining the ratio between (a) and (b).

There are no particular restrictions on the assay method for the type IV collagen high molecular form used, but an assay specific to the type IV collagen high molecular form is preferred, and an assay using an antibody specific for the type IV collagen high molecular form as according to the invention is even more preferred.

By determining the ratio between (a) and (b) it is possible to clarify the degree of liver fibrosis. For example, the value of (a)/(b) was correlated with increases in the grades through the aforementioned New Inuyama Classification, i.e. with progressing liver fibrosis. As mentioned above, 3 kinds of molecules are known as type IV collagen. As compared with measuring all of the molecular species of type IV collagen and taking the ratio of type IV collagen of a healthy person to the type IV collagen in the sample, a greater increase of the ratio will be obtained in proportion to the severity of liver fibrosis by using the type IV collagen high molecular form and determinating the ratio (a)/(b). By thus determining the value of (a)/(b) it is possible to make better decisions and diagnoses regarding the degree of fibrosis in liver.

According to the invention, it is possible to obtain the type IV collagen high molecular form which is considered to directly reflect the synthesis of type IV collagen in the liver, and to be more similar to the form that exist in the body. It is generally believed that in the initial stage of generation of liver fibrosis, the increase in collagen synthesis occurs first, prior to the increase in its degradation, and therefore the assay method of the invention makes it possible to detect the initial increase in collagen synthesis which allows us to begin the therapy earlier and with greater effect. In particular, interferon therapy is effective for chronic hepatitis but it is ineffective if the disease has progressed to liver cirrhosis. In addition, interferon therapy is more effective for earlier grades of liver fibrosis (Japanese Unexamined Patent Publication No. 8-334513). Thus, it is important to discover fibrosis in its early stage, and the assay system of the invention is effective for detecting early-stage fibrosis. In interferon therapy, the decision to allow the use of interferon lies generally between F2 and F3 of the New Inuyama Classification, and therefore it is important to use an assay method which can distinguish between F2 and F3 in particular, as according to the invention. The assay system of the invention can also be prepared as a kit.

Moreover, the invention is effective not only for detection of collagen synthesis but also for monitoring of the therapeutic effects by interferon and the like. That is, while obtained values become high in conventional assay methods even if the amount of collagen degradation has increased after the first treatment, according to the method of the invention which can detect collagen synthesis, it is believed that the determined value will decrease from the point at which the therapy begins, so that it will be possible to prevent unnecessary therapy and excess medicine.

EXAMPLES

The present invention will now be explained by way of examples. The invention is not, however, intended to be limited in any way by these examples. The monoclonal antibody 67 and the polyclonal antibody for type IV collagen used in the following examples are those described in Japanese Unexamined Patent Publication No. 8-100000.

Example 1

Preparation of Human Type IV Collagen Antigen

Using commercially available kits (products of Abbott Co.), 21 human full-term placentas (lyophilized) which had been confirmed to be HBV, HCV and HIV-1/2 negative were thawed, and after removal of the blood components by centrifugation, they were homogenized with a meat grinder to prepare a raw material with a wet weight of 6,500 g. This was suspended in a 4-fold volume (W/V) of a 10 mM Tris-HCl buffer, pH 7.5, 10 mM EDTA-3Na, and the suspension was stirred for 20 hours at 4° C. Next, the suspension was centrifuged 4200 rpm for 20 minutes at 4° C., using Beckman JS-4.2 rotor and the precipitate was collected. A 10 mM Tris-HCl buffer, pH 7.5, 10 mM EDTA-3Na was then used for washing the precipitate, which was repeated 3 times. Next, washing with a 4-fold volume (W/V) of a 50 mM Tris-HCl buffer, pH 7.5, 1.0 M NaCl, 10 mM EDTA-3Na and 0.5 M acetic acid was repeated 4 times each in the same manner, to obtain 13 Kg of washed material.

After suspending 1200 g of the washed material in 0.5 M acetic acid and adjusting the volume to 4,500 ml, 6 g of pepsin (product of Sigma Co.) was added and the reaction mixture was stirred for 120 hours at 4° C. for pepsin digestion. After centrifugation of the digested material, 15,000×G for 2 hours, at 4° C., 0.5 M acetic acid was added to the resulting supernatant to adjust back to 4,500 ml, the solution was stirred while adding 526 g of sodium chloride thereto, and the sodium chloride concentration was adjusted to 2.0 M, after which the mixture was further stirred for 20 hours at 4° C. to precipitate the solubilized collagen fraction. The suspension was centrifuged at 15,000×G, 2 hours, 4° C. to obtain a precipitate which was then suspended in 0.5 M acetic acid and dissolved while stirring for 20 hours at 4° C. This was centrifuged for 2 hours, at 4° C., 15,000×G and the protein concentration of the resulting supernatant was adjusted to 2.0 mg/ml with 0.5 M acetic acid. The protein concentration was determined by the Lowry method with a BSA standard (product of Biorad Co.) as reference.

Sodium chloride was added to the above-mentioned solubilized collagen solution while stirring to a final concentration of 0.7 M, and stirring was continued for 20 hours at 4° C. According to the aforementioned report by Sage et al. the type IV collagen is recovered in the supernatant at this point, but in order to obtain the more completed form of type IV collagen which is present in the body, the precipitate obtained by centrifugation at 15,000×G, 2 hours, 4° C. was recovered, again suspended in 0.5 M acetic acid, dissolved by stirring for 20 hours at 4° C. and then centrifuged under the same conditions as above to obtain a supernatant. After adjusting the protein concentration of the supernatant to 2.0 mg/ml with 0.5 M acetic acid, sodium chloride was again added to a final concentration of 0.7 M with stirring, and after further stirring for 20 hours at 4° C., the supernatant was obtained by centrifugation in the same manner. Sodium chloride was again added to the supernatant to a final concentration of 1.8 M and stirring was continued for 20 hours at 4° C.

The precipitate obtained by centrifuging 15,000×G for 2 hours at 4° C., was suspended in a 50 mM Tris-HCl buffer, pH 7.5 containing 1.0 M NaCl, and after adjusting the pH to 7.0 with 1.0 M NaOH and stirring for 2 hours at 4° C. for dissolution, it was dialyzed overnight at 4° C. against a 50 mM Tris-HCl buffer, pH 7.5, containing 1.0 M NaCl. The dialysate was centrifuged, 100,000×G for 30 minutes at 4° C. to obtain a supernatant, and after adjusting the protein concentration to 2.0 mg/ml with a 50 mM Tris-HCl buffer, pH 7.5, containing 1.0 M NaCl, sodium chloride was added to a final concentration of 2.0 M with stirring, and stirring was continued for 20 hours at 4° C. and followed by centrifugation under the same conditions as before to obtain a precipitate.

The precipitate was dissolved in 0.1 M acetic acid, and after dialysis overnight at 4° C. against 0.1 M acetic acid, the solution was centrifuged 100,000×G for 30 minutes at 4° C. After adjusting the protein concentration of the resulting supernatant to 1.0 mg/ml with 0.1 M acetic acid, sodium chloride was added to a final concentration of 0.2 M with stirring and stirring was continued for 20 hours at 4° C., after which the mixture was centrifuged 100,000×G for 30 minutes at 4° C., to obtain a supernatant, sodium chloride was added to a final concentration of 0.7 M, with stirring was continued for 20 hours at 4° C., and then the precipitate obtained from centrifugation in the same manner was again suspended in a 50 mM Tris-HCl buffer, pH 7.5, 1.0 M NaCl.

After adjusting the pH to 7.0 with 1.0 M NaOH and stirring for 2 hours at 4° C. for dissolution, the solution was dialyzed overnight at 4° C. against a 50 mM Tris-HCl buffer pH 7.5, 1.0 M NaCl. The supernatant obtained by centrifugation from this dialysate, 100,000×G for 30 minutes at 4° C. was adjusted to a protein concentration of 1.0 mg/ml with a 50 mM Tris-HCl buffer, pH 7.5, 1.0 M NaCl, after which sodium chloride was added to a final concentration of 1.3 M with stirring, and stirring was continued for 20 hours at 4° C. Sodium chloride was added to the supernatant obtained from centrifugation, to a final concentration of 2.0 M with stirring, and after further stirring for 20 hours at 4° C., the precipitate obtained by centrifugation in the same manner was dissolved in 10 mM acetic acid, and then the dialysate from overnight dialysis against 10 mM acetic acid at 4° C. was centrifuged for 30 minutes at 100,000×G, 4° C.

After adjusting the protein concentration of the resulting supernatant to 1.0 mg/ml with 10 mM acetic acid, it was dialyzed for 20 hours against a 50 mM Tris-HCl buffer, pH 8.6, 20 mM NaCl, 2.0 M urea at 4° C., and the supernatant obtained by centrifugation of the dialyzed solution 100,000×G for 30 minutes at 4° C., was dialyzed for 20 hours at 4° C. against a 5 mM Tris-HCl buffer pH 7.5, containing 2.0 M urea. The supernatant obtained by centrifugation of the dialyzed solution 100,000×G for 30 minutes at 4° C., was applied to DEAE-Sepharose column which had been equilibrized with a 5 mM Tris-HCl buffer, pH 7.5, containing 2.0 M urea, and after washing a 3 column-volume of the same buffer, it was eluted with the equilibrized buffer containing 150 mM NaCl. The absorbance at 230 nm was measured, in each fraction and the eluates corresponding to the peaks were pooled. Pooled material was dialyzed against 10 mM acetic acid and was followed by centrifugation 100,000×G for 30 minutes at 4° C., to obtain human type IV collagen (150 mg) containing the type IV collagen high molecular form in the supernatant.

Example 2

Purification of Human Type IV Collagen High Molecular Form

The type IV collagen obtained by the method described above was subjected to molecular weight fractionation to obtain the type IV collagen high molecular form.

After dialysis of 25 mg of the human type IV collagen obtained in Example 1 against 0.1 M acetic acid, sodium chloride was added to a final concentration of 4.5 M, and the precipitation was performed by stirring overnight at 4° C. The suspension was centrifuged for 30 minutes at 4° C., 100,000×G. After dissolving the precipitate in a 50 mM Tris-HCl buffer, pH 7.5, containing 1.0 M CaCl$_2$ followed by overnight dialysis against a 50 mM Tris-HCl buffer, pH 7.5, containing 1.0 M CaCl$_2$ at 25° C., heat treatment was carried out for 30 minutes at 45° C. The heat treated solution was centrifuged for 30 minutes at 25° C., 100,000×G, and the resulting supernatant was applied to a Superose 6 column which had been equilibrized with a 50 mM Tris-HCl buffer, pH 7.5, containing 1.0 M CaCl$_2$, for gel filtration at room temperature. The fractions which were eluted out in the void volume (up to the front of the initial peak) were pooled, and after dialysis using 10 mM acetic acid, was centrifuged for 30 minutes at 4° C., 100,000×G, and then was collected as a human type IV collagen high molecular form (3 mg).

Example 3
Construction of Assay System for Type IV Collagen High Molecular Form

Figure 1:
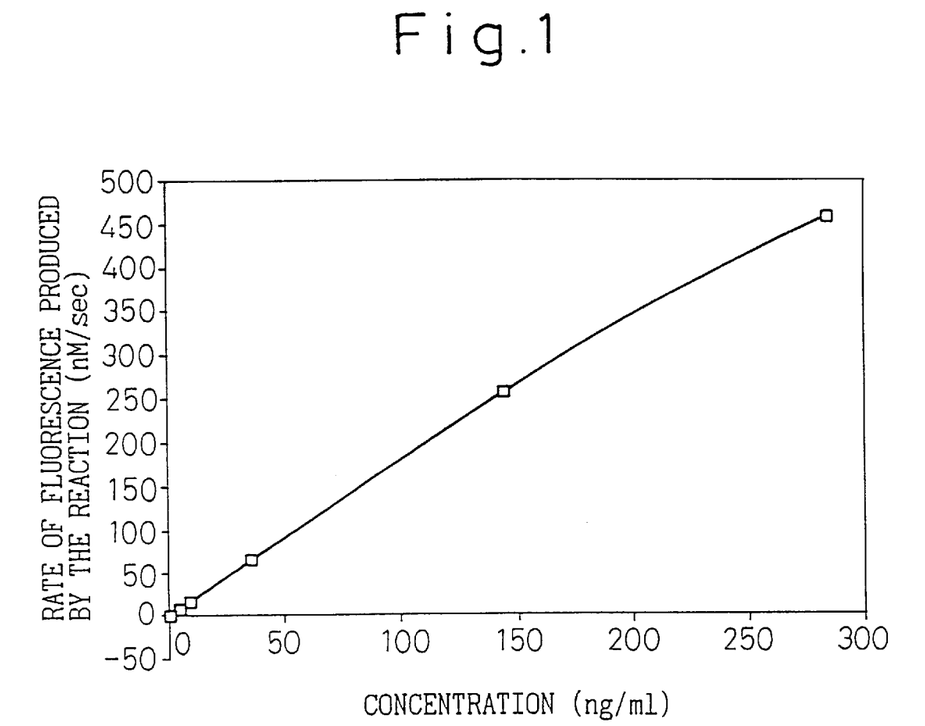
FIG. 1 is a graph showing a calibration curve for the assay system according to the invention, as obtained in Example 3.

Monoclonal antibody 67 was used to construct an assay system for the present invention, in the manner of Example 4 of Japanese Unexamined Patent Publication No. 8-100000. Briefly, a sandwich assay system was constructed using polystyrene beads as the solid phase, alkaline phosphatase as the labeling substance, monoclonal antibody 67 as the solid phase antibody and anti-type IV collagen polyclonal antibody as the labeled antibody. FIG. 1 shows the calibration curve obtained by measurement of the type IV collagen high molecular form at different concentrations prepared according to Example 2 in this assay system. FIG. 1 showed that this assay system was confirmed to be a type IV collagen high molecular form assay system.

Example 4
Evaluation of Reactivities for 7S Domain and Type IV Collagen High Molecular Form by the Assay System of the Invention and a Commercial Kit (A)

Figure 2:
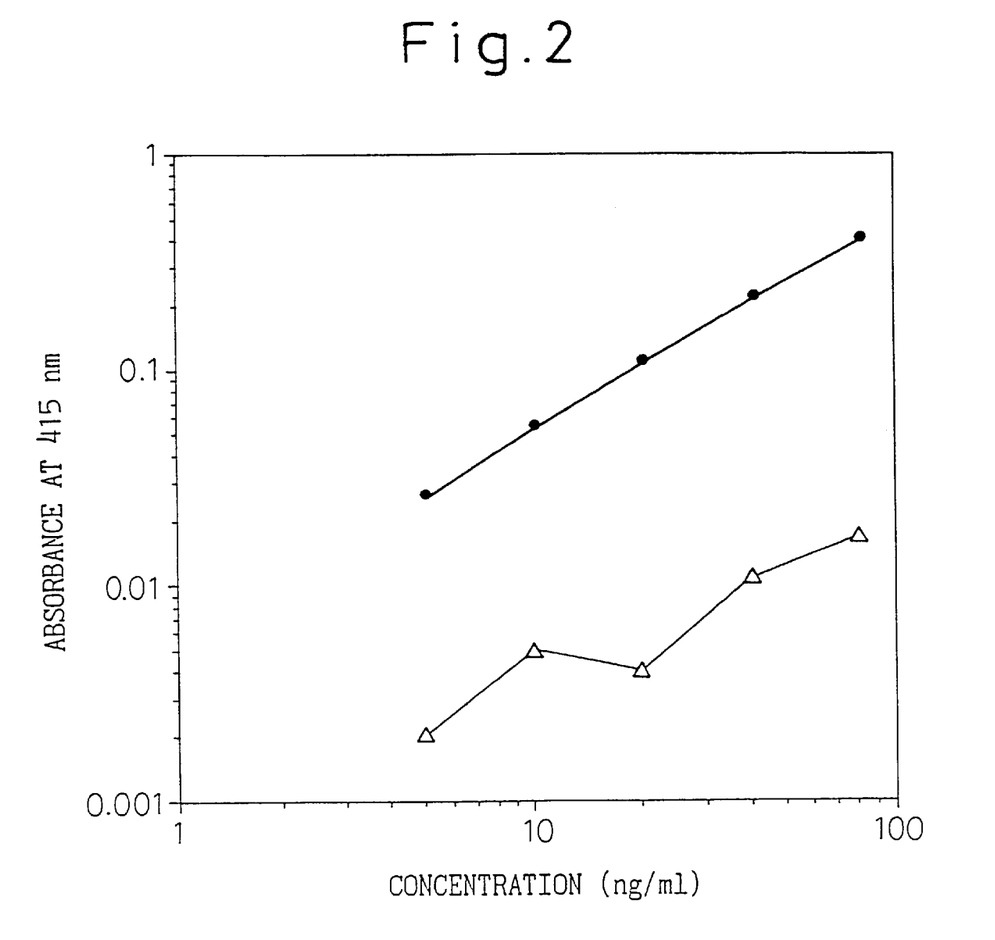
FIG. 2 is a graph showing the reactivity of the assay system of the invention for different antigens, as obtained in Example 4.
Figure 3:
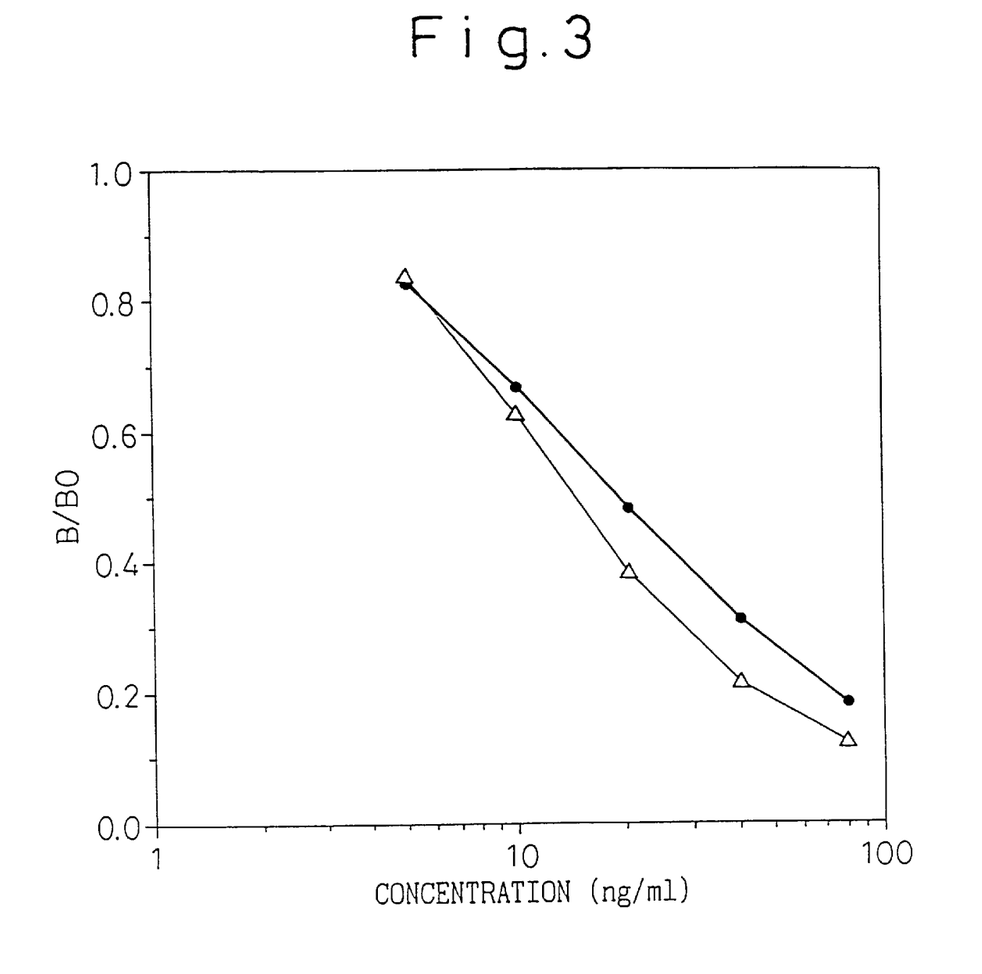
FIG. 3 is a graph showing the reactivity of the commercial kit (A) for different antigens, as obtained in Example 4.

The monoclonal antibody 67 was immobilized on a plate, and to each well there was added either the authentic 7S domain (calibrator of commercial kit (A)) or the type IV collagen high molecular form obtained in Example 2 at different concentrations for antigen-antibody reaction, and after washing, HRP-labeled rabbit anti-type IV collagen polyclonal antibody was added, the amount of HRP bound onto the well was quantified to examine the differences of antigens in reactivity were examined. The results are shown in FIG. 2. In this graph, the vertical axis indicates absorbance and the horizontal axis indicates the antigen concentration. The solid circles represent the type IV collagen high molecular form, and the triangles represent the 7S domain. These results demonstrated that the assay system of the invention reveals higher reactivity toward the type IV collagen high molecular form than toward the 7S domain, thus allowing more specific detection of the type IV collagen high molecular form. FIG. 3 shows the results of reactions using the same antigen in the commercial kit (A). Here as well, the solid circles represent the type IV collagen high molecular form, and the triangles represent the 7S domain. The vertical axis indicates B/B0, which is the ratio between the radioactive count in the bound product of the antigen-antibody reaction when antigen was added, to the radioactive count in the bound product without antigen. As clearly shown in FIG. 3, the type IV collagen high molecular form and the 7S domain exhibited almost equivalent reactivity in the commercial kit (A).

Figure 4:
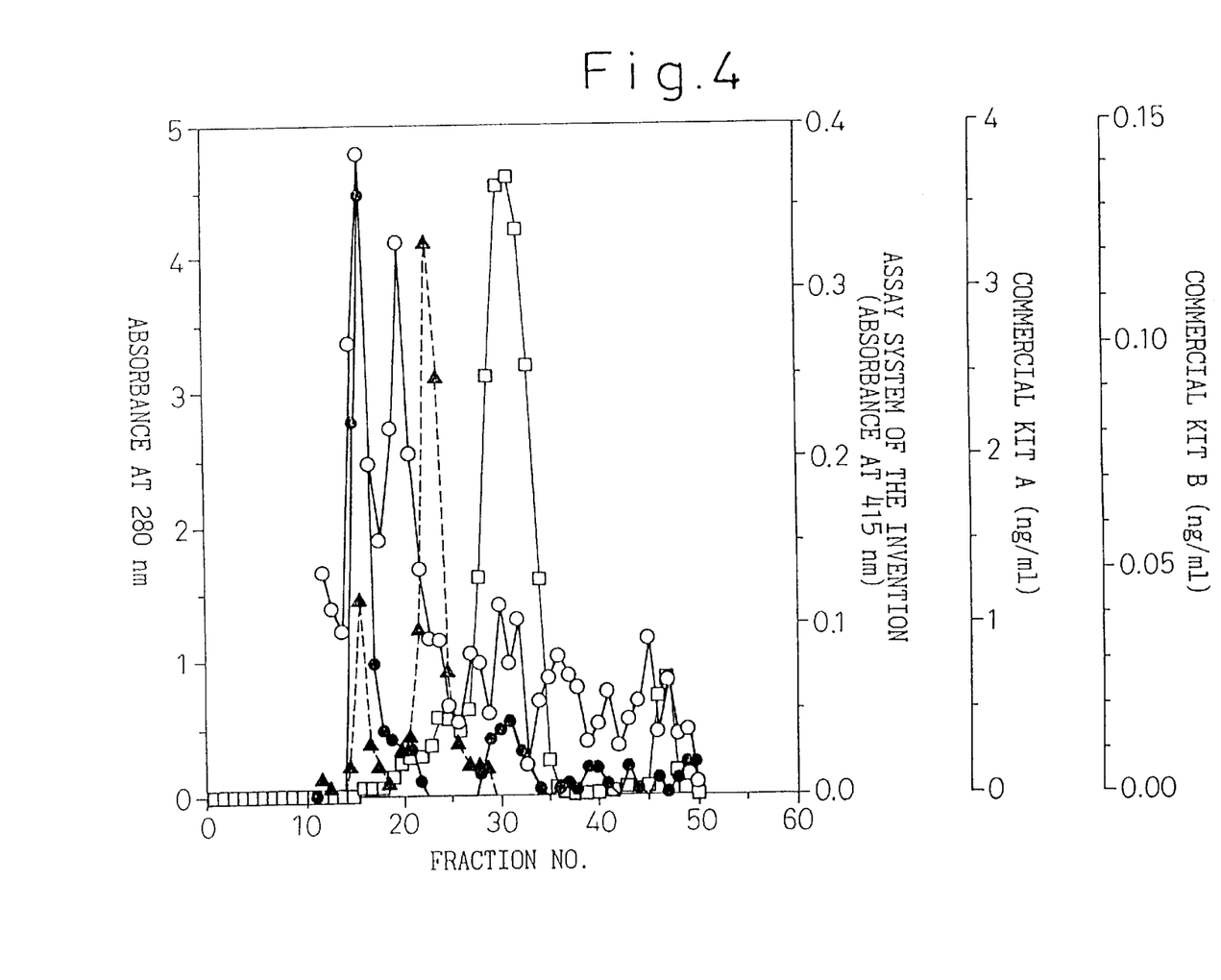
FIG. 4 is a graph showing the reactivities of the assay system of the invention and the commercial kits (A) and (B) for each fractions separated by gel filtration, as obtained in Example 5.

Example 5
Reactivity for Fraction Separated by Gel Filtration Chromatography of Human Serum A serum from a patient with liver cirrhosis was centrifuged for 10 minutes at 20° C., 15000 rpm, and a 0.2 ml portion of the supernatant was separated at room temperature using Superose 6 HR10/30 which had been equilibrized with a 100 mM Tris-HCl buffer, pH 7.5, containing 150 mM NaCl, and a comparison was made in terms of reactivity with the assay system of the invention according to Example 4, commercial kit (A) and another commercial type IV collagen assay kit (Panassay IV·C, Daiichi Chemicals, hereunder referred to as "commercial kit (B)"). The results are shown in FIG. 4. In this graph, the squares represent the absorbance at 280 nm, the solid circles represent the results using the assay system of the invention, the outlined circles represent the results using kit (A) and the triangles represent kit (B).

As shown in FIG. 4, both the type IV collagen high molecular form and the 7S domain (molecular weight 23 K) are detected with the commercial kit (A), as described in the aforementioned report by Murawaki et al., and antigenicity related to 7S collagen appeared in 2 peaks. It was found that the commercial kit (B) recognizes only smaller molecules than 7S domain. In contrast, the present assay system achieves specific detection for the type IV collagen high molecular form which has a larger molecular weight than that of 7S domain, and the position of this peak was coincided with the peaks of the commercial kit (A). Since this peak of the type IV collagen high molecular form reflects the amount of type IV collagen synthesized in the liver, the assay method of the invention which specifically detects the type IV collagen high molecular form can be considered to be an assay system which more accurately reflects the generation of type IV collagen.

Example 6
Clinical Study Using the Assay System of the Invention which Specifically Detects the Type IV Collagen High Molecular Form The assay system of the invention according to Example 3 was used for measurement of the type IV collagen high molecular form using serum obtained from patients with liver diseases, and the results were compared with the degree of liver fibrosis according to histological diagnosis by liver biopsy. A total of 164 subjects were classified according to the New Inuyama Classification indicating the degree of liver fibrosis as follows: F0+F1: 47 cases, F2: 43 cases, F3: 27 cases, F4: 47 cases. The mean values and standard deviations for these groups are listed in Table 1.

TABLE 1

| Classification | No. of cases | Mean concentration (ng/ml) | Standard deviation (ng/ml) |
| --- | --- | --- | --- |
| F0 & F1 | 47 | 10.34 | 5.317 |
| F2 | 43 | 12.99 | 5.053 |
| F3 | 27 | 20.38 | 8.692 |
| F4 | 47 | 39.55 | 24.518 |

Table 1 shows that the assay values for the type IV collagen high molecular form according to the present invention increase with the progression of liver fibrosis, i.e. from F0+F1 to F4. The Fisher analysis was also used to assess whether a statistical significant difference existed between the groups. The results are shown in Table 2.

TABLE 2

| | | Significance level of 5% | | | |
| --- | --- | --- | --- | --- | --- |
| Reference groups | Comparison groups | Difference in mean values | Ignored value | p value | Significant difference |
| F0 & F1 | F2 | −2.648 | 5.893 | 0.3762 | no |
| F0 & F1 | F3 | −10.043 | 6.743 | 0.0038 | yes |
| F0 & F1 | F4 | −29.207 | 5.760 | <0.0001 | yes |
| F2 | F3 | −7.395 | 6.857 | 0.0347 | yes |
| F2 | F4 | −26.559 | 5.893 | <0.0001 | yes |
| F3 | F4 | −19.164 | 6.743 | <0.0001 | yes |

Table 2 shows that while no significant difference was found between F0+F1 and F2, significant differences were found between the other groups, i.e. between F0+F1 and F3, between F0+F1 and F4, between F2 and F3, between F2 and F4 and between F3 and F4. Thus, the assay system of the present invention allows distinction to be made between these groups, so that the degree of liver fibrosis can be diagnosed. In particular, the assay system of the present invention makes it possible for the first time to distinguish between F2 and F3, which cannot be distinguished according to conventional assay methods.

Figure 5:
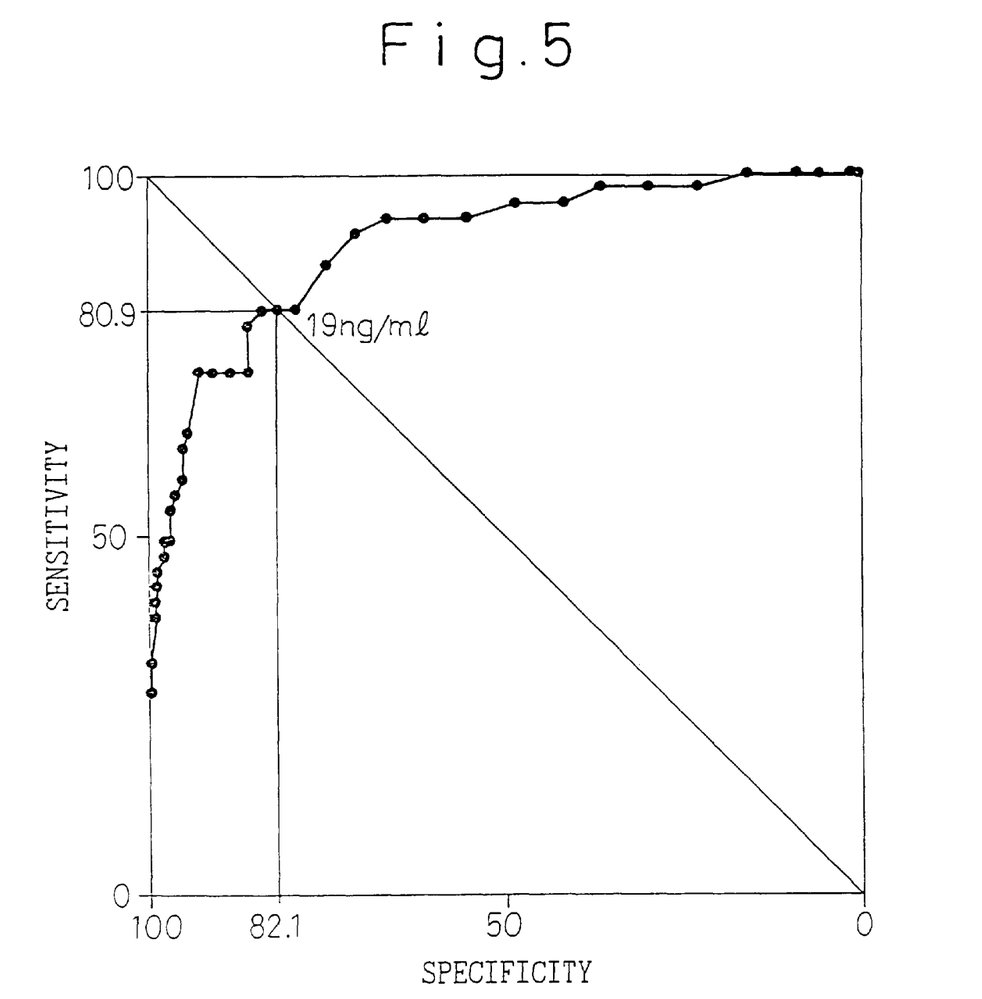
FIG. 5 is a graph showing the ROC curve obtained in Example 6.

With an ROC curve for F3 and F4 (corresponding to the conventional distinction between chronic active hepatitis and liver cirrhosis), serum high molecular form type IV collagen concentration was 82.1% specific and 80.9% sensitive at the cutoff value of 19 ng/ml as shown in FIG. 5, indicating equivalent performance as compared to the values with kit (A) described in the aforementioned report by Murawaki et al. (specificity: 88%, sensitivity: 83%, cutoff 9 ng/ml).

Example 7
Clinical Study Using the Assay System of this Invention (2)

Serum was collected from patients with liver diseases and measured using the method according to Example 3 of the present invention or using the commercial kit (A). A total of 199 subjects were classified according to the New Inuyama Classification indicating the degree of liver fibrosis as follows: Healthy: 33 cases, F0+F1: 47 cases, F2: 43 cases, F3: 29 cases, F4: 47 cases. The mean values and standard deviations for these groups are listed in Table 3.

TABLE 3

| Classification | No. of cases | Assay values according to the present invention | | Assay values according to commercial kit (A) | |
| --- | --- | --- | --- | --- | --- |
| | | Mean value (ng/ml) | Standard deviation | Mean value (ng/ml) | Standard deviation |
| Healthy | 33 | 5.79 | 1.48 | 4.03 | 0.59 |
| F0 + F1 | 47 | 10.54 | 5.27 | 4.78 | 1.59 |
| F2 | 43 | 12.99 | 5.05 | 5.24 | 1.49 |
| F3 | 29 | 20.08 | 8.45 | 6.60 | 1.62 |
| F4 | 47 | 40.13 | 24.12 | 11.81 | 5.17 |

As shown in Table 3, the mean values with the assay method of the present invention indicated a greater increase in assay values in proportion to the degree of liver fibrosis compared to those with commercial kit (A). This is believed to be due to the more specific detection of the type IV collagen high molecular form by the method of the present invention than by the commercial kit (A).

The results in Table 3 were used as the basis for a statistical t test to assess whether significant differences existed in the values of the different groups. Table 4 shows the results for the invention, and Table 5 shows the results for the commercial kit (A).

TABLE 4

Significance level of 5%

| Reference groups | Comparison groups | Difference in mean values | t value | t limit value (both ends) | p value | Significant difference |
| --- | --- | --- | --- | --- | --- | --- |
| Healthy | F0 + F1 | −4.88 | −6.088 | 2.006 | <0.0001 | yes |
| Healthy | F2 | −7.33 | −9.122 | 2.010 | <0.0001 | yes |
| Healthy | F3 | −14.42 | −9.091 | 2.045 | <0.0001 | yes |
| Healthy | F4 | −34.47 | −9.776 | 2.013 | <0.0001 | yes |

TABLE 4-continued

Significance level of 5%

| Reference groups | Comparison groups | Difference in mean values | t value | t limit value (both ends) | p value | Significant difference |
| --- | --- | --- | --- | --- | --- | --- |
| F0 + F1 | F2 | −2.65 | −1.807 | 1.988 | 0.074 | no |
| F0 + F1 | F3 | −9.54 | −6.070 | 1.993 | <0.0001 | yes |
| F0 + F1 | F4 | −29..59 | −8.216 | 1.986 | <0.0001 | yes |
| F2 | F3 | −7.64 | −4.902 | 1.995 | <0.0001 | yes |
| F2 | F4 | −27.69 | −7.237 | 1.988 | <0.0001 | yes |
| F3 | F4 | −20.05 | −4.306 | 1.993 | <0.0001 | yes |

TABLE 5

Significance level of 5%

| Reference groups | Comparison groups | Difference in mean values | t value | t limit value (both ends) | p value | Significant difference |
| --- | --- | --- | --- | --- | --- | --- |
| Healthy | F0 + F1 | −0.80 | −3.181 | 2.002 | 0.0024 | yes |
| Healthy | F2 | −1.26 | −5.156 | 2.004 | <0.0001 | yes |
| Healthy | F3 | −2.62 | −8.048 | 2.042 | <0.0001 | yes |
| Healthy | F4 | −7.84 | −9.649 | 2.020 | <0.0001 | yes |
| F0 + F1 | F2 | −0.46 | −1.405 | 1.988 | 0.164 | no |
| F0 + F1 | F3 | −1.82 | −4.657 | 2.005 | <0.0001 | yes |
| F0 + F1 | F4 | −7.04 | −8.786 | 1.988 | <0.0001 | yes |
| F2 | F3 | −1.36 | −3.523 | 2.007 | 0.0009 | yes |
| F2 | F4 | −6.63 | −7.892 | 1.990 | <0.0001 | yes |
| F3 | F4 | −5.22 | −5.072 | 1.997 | <0.0001 | yes |

The analysis of the t test showed significant differences exist in the results obtained by both the present invention and the commercial kit (A) for all tests except the test between the F0+F1 group and the F2 group. For the analysis between the F0+F1 group and the F2 group, when the p values for the present invention and the commercial kit (A) were compared, the assay of the present invention gave a markedly lower p value, indicating that the assay of the present invention more precisely reflects the difference in histological conditions between the F0+F1 group and the F2 group. For distinction between the F2 group and F3 group as well, the p value was less than 0.0001 for the present invention but 0.0009 for the commercial kit (A), indicating that the present invention more precisely reflects the difference in histological conditions between the F2 group and F3 group. From these results it is obvious that measurement of the type IV collagen high molecular form according to the present invention reflects the degree of progression of liver fibrosis more accurately than the commercial kit (A), and can therefore give a better indicator for assessing the progression of liver fibrosis without biopsy.

Example 8
Clinical Study Using the Assay System of this Invention (3)

The values in Table 3 of Example 7 were used as the basis for determining the ratios (a)/(b) for (a): the type IV collagen high molecular form in samples of each group and (b): the type IV collagen high molecular form of the healthy person, according to the assay method of the present invention. The ratios (a')/(b') for (a'): the values for each group and (b'): the value for the healthy person using the commercial kit (A) were also determined. The results are shown in Table 6.

TABLE 6

| Classification | Ratio to assay value for healthy person | |
| --- | --- | --- |
| | Present invention | Commercial kit (A) |
| Healthy | 1.00 | 1.00 |
| F0 + F1 | 1.82 | 1.19 |
| F2 | 2.24 | 1.30 |
| F3 | 3.47 | 1.64 |
| F4 | 6.93 | 2.93 |

As clearly seen from Table 6, the ratios (a)/(b) for the present invention showed higher increases in value in proportion to the degree of liver fibrosis, as compared to the ratios (a')/(b') determined with the commercial kit (A), thus better reflecting the progression of liver fibrosis. Consequently, distinction and diagnosis of degrees of liver fibrosis can be more clearly provided in early stages by determining the ratio (a)/(b) according to the present invention. Presumably this is because the assay according to the present invention specifically detects the type IV collagen high molecular form while the assay with the commercial kit (A) detects both the type IV collagen high molecular form and the 7S domain, as shown in Examples 4 and 5. It is therefore seen that it is important to determine the ratio based on the method which can specifically detect the type IV collagen high molecular form.

What is claimed is:

1. A type IV collagen high molecular form having the following properties:
   (a) having a molecular weight higher than that of the 7S domain of type IV collagen;
   (b) having the 7S domain in its structure;
   (c) being recovered from a collagen solution digested by pepsin in the following steps:
      (1) salt precipitating said solution with sodium chloride at a concentration of at least 2 M, thereby forming a supernatant and a precipitate,
      (2) dissolving the precipitate obtained from step (1), to form a second solution,
      (3) salt precipitating said second solution with sodium chloride at a concentration no higher than 1.2 M, thereby forming a supernatant and a precipitate,
      (4) dissolving the precipitate obtained from step (3), to form a third solution,
      (5) salt precipitating said third solution with sodium chloride at a concentration no higher than that used in step (3), thereby forming a supernatant and a precipitate, and
      (6) collecting the supernatant of step (5).

2. The type IV collagen high molecular form of claim 1, wherein the type IV collagen high molecular form is able to be specifically bound by a monoclonal antibody produced by the hybridoma COL IV-67 (FERM BP-5240).

3. A process for producing a type IV collagen high molecular form, comprising the steps of:
   (1) salt precipitating said solution with sodium chloride at a concentration of at least 2 M, thereby forming a supernatant and a precipitate,
   (2) dissolving the precipitate obtained from step (1), to form a second solution,
   (3) salt precipitating said second solution with sodium chloride at a concentration no higher than 1.2 M, thereby forming a supernatant and a precipitate,
   (4) dissolving the precipitate obtained from step (3), to form a third solution,
   (5) salt precipitating said third solution with sodium chloride at a concentration no higher than that used in step (3), thereby forming a supernatant and a precipitate, and
   (6) collecting the supernatant of step (5).

4. The process of claim 3, wherein the type IV collagen high molecular form is able to be specifically bound by a monoclonal antibody produced by the hybridoma COL IV-67 (FERM BP-5240).

5. A method for measuring the concentration of a type IV collagen high molecular form, comprising the step of reacting an antibody that specifically binds the type IV collagen high molecular form of claim 1 with type IV collagen high molecular form in a sample.

6. The method of claim 5, wherein said antibody is a monoclonal antibody produced by the hybridoma COL IV-67 (FERM BP-5240).

7. A kit used for measuring a type IV collagen high molecular form, comprising an antibody that specifically binds to the type IV collagen high molecular form of claim 1.

8. The kit of claim 7, wherein said antibody that specifically binds to the type IV collagen high molecular form is a monoclonal antibody produced by the hybridoma COL IV-67 (FERM BP-5240).

9. A method for diagnosing the degree of liver fibrosis, comprising the steps of measuring the concentration of type IV collagen high molecular form in a sample using the method of claim 5, and relating the measurement to the degree of liver fibrosis wherein as the measured concentration is higher the degree of liver fibrosis is higher.

10. The method of claim 9, wherein said antibody that specifically binds to the type IV collagen high molecular form is a monoclonal antibody produced by the hybridoma COL IV-67 (FERM BP-5240).

11. A method for measuring a type IV collagen high molecular form, comprising the steps of:
    (a) measuring concentration of type IV collagen high molecular form in a sample,
    (b) measuring concentration of type IV collagen high molecular form in a healthy person, and
    (c) determining the ratio between (a) and (b).

12. The method of claim 11, wherein the type IV collagen high molecular form is able to be specifically bound by a monoclonal antibody produced by the hybridoma COL IV-67 (FERM BP-5240).

13. A method for diagnosing the degree of liver fibrosis, comprising the steps of measuring the type IV collagen high molecular form in a sample using the method of claim 11, and relating the ratio (a)/(b) with the degree of liver fibrosis wherein as the ratio (a)/(b) is higher, the degree of liver fibrosis is higher.

14. The method of claim 13, wherein the type IV collagen high molecular form is able to be specifically bound by a monoclonal antibody produced by the hybridoma COL IV-67 (FERM BP-5240).

* * * * *